United States Patent [19]

Pasquale

[11] Patent Number: 4,628,051
[45] Date of Patent: * Dec. 9, 1986

[54] TRIPHASIC ORAL CONTRACEPTIVE

[75] Inventor: Samuel A. Pasquale, Basking Ridge, N.J.

[73] Assignee: Ortho Pharmaceutical Corporation, Raritan, N.J.

[*] Notice: The portion of the term of this patent subsequent to Oct. 1, 2002 has been disclaimed.

[21] Appl. No.: 743,344

[22] Filed: Jun. 11, 1985

Related U.S. Application Data

[63] Continuation-in-part of Ser. No. 607,038, May 4, 1984, Pat. No. 4,544,554, which is a continuation-in-part of Ser. No. 536,135, Sep. 26, 1983, Pat. No. 4,530,839.

[51] Int. Cl.$^4$ .................... A61K 31/56; A01N 45/00
[52] U.S. Cl. .................................. 514/170; 514/177; 514/182
[58] Field of Search ........................ 514/170

[56] References Cited

U.S. PATENT DOCUMENTS 4,530,839 7/1985 Pasquale .............................. 514/171
4,544,554 10/1985 Pasquale .............................. 514/170

Primary Examiner—Elbert L. Roberts
Attorney, Agent, or Firm—Benjamin F. Lambert

[57] ABSTRACT

A method of contraception in which an estrogen and a progestogen are administered daily in a three phase sequence for 21 days is disclosed. In the first phase a combination of an estrogen and a progestogen in a low but contraceptively effective daily dosage corresponding in estrogenic activity to 0.02–0.05 mg of 17α-ethinylestradiol and in progestogenic activity to 0.065–0.75 mg of norethindrone is administered for 5–8 days; followed by the administering of the same dosage of estrogen and a progestogen corresponding in progestogenic activity to 0.25–1.0 mg of norethindrone for 7–11 days; followed by the administering of the same dosage of estrogen and a progestogen corresponding in progestogenic activity to 0.35–2.0 mg of norethindrone for 3–7 days; followed by 6–8 days without administering either an estrogen or a progestogen.

25 Claims, No Drawings

TRIPHASIC ORAL CONTRACEPTIVE

This is a continuation-in-part of application Ser. No. 607,038, filed May 4, 1984, now U.S. Pat. No. 4,544,554 which in turn is a continuation-in-part of application Ser. No. 536,135 filed Sept. 26, 1983. now U.S. Pat. No. 4,530,839.

This invention relates to a method of effecting contraception in the human female. More particularly, this invention relates to a method of effecting contraception comprising the oral administration of a low but contraceptively effective daily dosage of a combination of an estrogen and a progestogen for 21 successive days.

Oral contraceptives first became available in the early 1960's. Since that time, a number of regimens for controlling ovulation and conception by the administration of hormones have become known and are readily available. The oral administration of combination type preparations containing both an estrogen and a progestogen has been known for some time. Some of these regimens are based upon consistent dosage of either an estrogen or progestogen or both throughout the period of administration while others are directed to regimens wherein the amount of estrogen or progestogen or both is increased or decreased during the menstrual cycle.

One disadvantage inherent in the administration of the aforementioned pure and modified sequential products involving the administration of relatively high doses of estrogen, in addition to the usual symptoms due to excessive estrogen, i.e., gastrointestinal disturbances, nausea, weight gain with formation of edema, etc., is an increase in the risk of thromboembolic disease. Many of these disadvantages can be avoided by the administration of two-stage or biphasic combination contraceptives, but even in the biphasic products it would be desirable if the ability to control the cycle could be improved.

The administration of three-stage or triphasic combination type oral contraceptives is also known. Triphasic combinations of various types are described in U.S. Pat. Nos. 4,390,531; 4,066,757; 3,957,982; 3,795,734; and 2,431,704.

In recent years data collected on the use of various oral contraceptive regimens have indicated that increased blood pressure and decreased glucose tolerance are associated with the progestogen content or progestational activity of oral contraceptives. In addition, the progestogen activity is associated with a decrease in serum high density lipoprotein values. These findings have prompted a greater emphasis on a reduction of the progestogen dosage in oral contraceptives.

There is a need, therefore, for a combination type contraceptive which contains low concentrations of estrogen and progestogen but is still effective for the prevention of pregnancy.

By the present invention a triphasic oral contraceptive regimen is provided wherein the estrogen dosage is kept constant throughout the 21-day cycle while the progestogen dosage is gradually increased in successive doses. The purpose of the invention is to lower the total monthly steroid dose in the oral contraceptive while still obtaining equivalent bleeding patterns and protection against pregnancy as found with conventional oral contraceptives.

According to the present invention, reliable contraception is achieved by administering for 21 successive days to a female a combination of an estrogen and a progestogen, for the first 5–8 days in a contraceptively effective daily dosage a progestogen equivalent in effect to about 0.065–0.75 mg of norethindrone in combination with an estrogen equivalent in effect to about 0.02–0.05 mg of ethinyl estradiol; followed by the administration for 7–11 days, of a daily dosage of a progestogen equivalent in effect to about 0.25–1.0 mg of a norethindrone together with an estrogen equivalent in effect to about 0.02–0.50 mg of ethinyl estradiol; and followed by the administration for 3–7 days of a daily dosage of a progestogen equivalent in effect to about 0.35–2.0 mg of norethindrone in combination with an estrogen equivalent in effect to about 0.02–0.05 mg of ethinyl estradiol, provided that the dosage of estrogen is kept constant in each phase during the 21-day cycle. The actual weight amount of the dosage at each dosage level will depend upon the estrogenic and progestogenic activity, respectively, of the components selected for the dosage units.

The total number of days during which the progestogen and estrogen combinations are administered daily is 21. These are followed by 6–8 days which are free of hormone administration to approximate the natural 28-day menstrual cycle of the female. Day one of the cycle is defined as the first day of menstruation and the days are numbered sequentially thereafter until menstruation occurs again. The cycle usually lasts 28 days but it may be slightly longer or shorter. In actual practice a placebo or any other hormone-free agent such as, for example, iron supplements, may be administered during this period. Thus, in a preferred regimen, phase one would commence sometime between day 4 and day 6 of the menstrual cycle and last 5–8 days but preferably 7 days, phase two would last 7–11 days, preferably 7 days, while phase three would last 3 to 7 days, preferably 7 days.

The contraceptive composition employed in the present invention comprises 21 separate daily dosage units which are adapted for successive daily oral ingestion. The composition consists essentially of, as the first phase, 5–8 dosage units containing, in admixture with a pharmaceutically acceptable carrier, a combination of an estrogen in combination with a progestogen, followed by, as the second phase, 7–11 dosage units containing, a combination of an estrogen and a progestogen, followed by, as the third phase, 3–7 dosage units containing a combination of an estrogen and a progestogen followed by 6–8 dosage units free of estrogen and progestogen. The estrogen daily dosage is kept constant in all three phases.

Any conventional estrogen may be employed as a suitable component in the contraceptive regimen of this invention. The particular regimen employed in a daily dosage should be equal in contraceptive activity in each phase to a daily dosage of about 0.020–0.050 mg of 17α-ethinylestradiol. The preferred dosage is one equal to a daily dosage of about 0.035 mg of 17α-ethinylestradiol.

In addition to 17α-ethinylestradiol, esters and ethers of 17α-ethinylestradiol such as, for example, 17α-ethinylestradiol 3-dimethylamino propionate, 17α-ethinylestradiol 3-cyclopentyl ether (quinestrol) and 17α-ethinylestradiol 3-methyl ether (mestranol) may also be employed as the estrogen component. Natural estrogens such as estrone, estrone sulfate, estrone sulfate piperazine salt, estradiol and estriol, and their esters, as well as the synthetic estrogens, may also be employed. The preferred estrogens are 17α-ethinylestradiol and 17α-ethinylestradiol 3-methyl ether.

As the progestogen component, any progestationally active compound may be employed. The progestogen is preferably administered in a daily dosage in the first phase corresponding in progestogenic activity to 0.065–0.75 mg of norethindrone per day, during the next phase a daily dosage corresponding in progestogenic activity to 0.25–1.0 mg of norethindrone per day and during the third phase a daily dosage corresponding in progestogenic activity to 0.35–2.0 mg of norethindrione per day.

Progestogens which may be employed as a component in the present invention include progesterone and its derivatives such as, for example, 17-hydroxyprogesterone esters and 19-nor-17-hydroxyprogesterone esters, 17α-ethinyltestosterone, 17α-ethinyl-19-nortestosterone and derivatives thereof, norethindrone, D-norgestrel, $\Delta^{15}$ levonorgestrel, $\Delta^{15}$ levonorgestrel acetate, $\Delta^{15}$ levonorgestrel acetate oxime, and D-17β-acetoxy-13β-ethyl-17α-ethinyl-gon-4-en-3-one oxime. The preferred progestogens are norethindrone, D-norgestrel and D-17β-acetoxy-13β-ethyl-17α-ethinyl-gon-4-en-3-one oxime (norgestimate).

The estrogen and progestogen components are preferably administered together orally in a pharmaceutically acceptable nontoxic carrier, but they can also be administered separately or parenterally. In general, the effective agents are processed, together with the usual additives, vehicles and/or flavor-ameliorating agents normally employed in Galenic pharmacy, in accordance with generally accepted pharmaceutical practices. For the preferred oral administration, tablets, dragees, capsules, pills, suspensions or solutions are particularly suitable; for parenteral application, oily solutions such as, for example, sesame oil or castor oil solutions which can optionally additionally contain a diluent such as, for example, benzyl benzoate or benzyl alcohol.

In the case of the preferred oral application, the three-phase combination-type contraceptives are preferably packaged in the form of a pharmaceutical kit or package in which the daily dosages are arranged for proper sequential administration. This invention also relates, therefore, to a pharmaceutical unit which contains combination-type contraceptives in 28 dosage units in a synchronized, fixed sequence, wherein the sequence or arrangement of the dosage units corresponds to the stages of daily administration.

The pharmaceutical unit can be, e.g., in the form of a transparent package having 28 dosage units arranged sequentially and consisting of 7 tablets for the first phase, followed by 7 tablets for the second phase, followed by 7 tablets for the third phase, and finally followed by 7 placebos. A single tablet is to be taken each day over a period of 28 days.

Without further elaboration it is believed that one skilled in the art, using the preceding description, can fully utilize the present invention. The following preferred specific embodiments are to be construed as merely illustrative of the invention and are not meant to limit the invention in any way.

EXAMPLE 1

Composition of a tablet for each stage:

| | 1st Stage 7 Tablets |
|---|---|
| 0.035 mg. | 17α-ethinylestradiol |
| 0.50 mg. | norethindrone |
| 88.9 mg. | lactose anhydrous |
| 10.0 mg. | pregelatanized starch N.F. |
| 0.5 mg. | magnesium stearate N.T. |
| 99.935 mg. | total weight |
| | 2nd Stage 7 Tablets |
| 0.035 mg. | 17α-ethinylestradiol |
| 0.75 mg. | norethindrone |
| 88.70 mg. | lactose anhydrous |
| 10.02 mg. | pregelatanized starch N.F. |
| 0.5 mg. | magnesium stearate N.F. |
| 100.005 mg. | total weight |
| | 3rd Stage 7 Tablets |
| 0.035 mg. | 17α-ethinylestradiol |
| 1.0 mg. | norethindrone |
| 88.5 mg. | lactose anhydrous |
| 10.0 mg. | pregelatanized starch N.F. |
| 0.5 mg. | magnesium stearate N.F. |
| 100.035 mg. | total weight |

EXAMPLE 2

Composition of a tablet for each stage:

| | 1st Stage 7 Tablets |
|---|---|
| 0.035 mg. | 17α-ethinylestradiol |
| 0.50 mg. | D-17β-acetoxy-13β-ethyl-17α-ethinyl-gon-4-en-3-one oxime |
| 87.9 mg. | lactose anhydrous |
| 11.1 mg. | pregelatanized starch N.F. |
| 0.5 mg. | magnesium stearate N.F. |
| 100.035 mg. | total weight |
| | 2nd Stage 7 Tablets |
| 0.035 mg. | 17α-ethinylestradiol |
| 0.75 mg. | D-17β-acetoxy-13β-ethyl-17α-ethinyl-gon-4-en-3-one oxime |
| 89.70 mg. | lactose anhydrous |
| 9.02 mg. | pregelatanized starch N.F. |
| 0.5 mg. | magnesium stearate N.F. |
| 100.005 mg. | total weight |
| | 3rd Stage 7 Tablets |
| 0.035 mg. | 17α-ethinylestradiol |
| 1.0 mg. | D-17β-acetoxy-13β-ethyl-17α-ethinyl-gon-4-en-3-one oxime |
| 87.5 mg. | lactose anhydrous |
| 11.0 mg. | pregelatanized starch N.F. |
| 0.5 mg. | magnesium stearate N.F. |
| 100.035 mg. | total weight |

EXAMPLE 3

Composition of a tablet for each stage:

| | 1st Stage 7 Tablets |
|---|---|
| 0.035 mg. | 17α-ethinylestradiol |
| 0.50 mg. | D-norgestrel |
| 90.0 mg. | lactose anhydrous |
| 9.0 mg. | pregelatanized starch N.F. |
| 0.5 mg. | magnesium stearate N.F. |
| 100.035 mg. | total weight |
| | 2nd Stage 7 Tablets |
| 0.035 mg. | 17α-ethinylestradiol |
| 0.75 mg. | D-norgestrel |
| 87.70 mg. | lactose anhydrous |
| 11.02 mg. | pregelatanized starch N.F. |
| 0.5 mg. | magnesium stearate N.F. |
| 100.005 mg. | total weight |
| | 3rd Stage 7 Tablets |
| 0.035 mg. | 17α-ethinylestradiol |
| 1.0 mg. | D-norgestrel |
| 89.5 mg. | lactose anhydrous |
| 9.0 mg. | pregelatanized starch N.F. |
| 0.5 mg. | magnesium stearate N.F. |

EXAMPLE 4

Composition of a tablet for each stage:

| | 1st Stage 7 Tablets |
|---|---|
| 0.035 mg. | 17α-ethinylestradiol |
| 0.180 mg. | norgestimate |
| 90.200 mg. | lactose anhydrous |
| 9.085 mg. | pregelatanized starch N.F. |
| 0.500 mg. | magnesium stearate N.F. |
| 100.000 mg. | total weight |
| | 2nd Stage 7 Tablets |
| 0.035 mg. | 17α-ethinylestradiol |
| 0.215 mg. | norgestimate |
| 90.150 mg. | lactose anhydrous |
| 9.100 mg. | pregelatanized starch N.F. |
| 0.500 mg. | magnesium stearate N.F. |
| 100.000 mg. | total weight |
| | 3rd Stage 7 Tablets |
| 0.035 mg. | 17α-ethinylestradiol |
| 0.250 mg. | norgestimate |
| 90.115 mg. | lactose anhydrous |
| 9.100 mg. | pregelatanized starch N.F. |
| 0.500 mg. | magnesium stearate N.F. |
| 100.000 mg. | total weight |

EXAMPLE 5

Composition of a tablet for each stage:

| | 1st Stage 7 Tablets |
|---|---|
| 0.035 mg. | 17α-ethinylestradiol |
| 0.250 mg. | norethindrone |
| 88.9 mg. | lactose anhydrous |
| 10.32 mg. | pregelatanized starch N.F. |
| 0.5 mg. | magnesium stearate N.F. |
| 100.005 mg. | total weight |
| | 2nd Stage 7 Tablets |
| 0.035 mg. | 17α-ethinylestradiol |
| 0.375 mg. | norethindrone |
| 88.70 mg. | lactose anhydrous |
| 10.39 mg. | pregelatanized starch N.F. |
| 0.5 mg. | magnesium stearate N.F. |
| 100.000 mg. | total weight |
| | 3rd Stage 7 Tablets |
| 0.035 mg. | 17α-ethinylestradiol |
| 0.500 mg. | norethindrone |
| 88.5 mg. | lactose anhydrous |
| 10.47 mg. | pregelatanized starch N.F. |
| 0.5 mg. | magnesium stearate N.F. |
| 100.005 mg. | total weight |

EXAMPLE 6

Composition of a tablet for each stage:

| | 1st Stage 7 Tablets |
|---|---|
| 0.035 mg. | 17α-ethinylestradiol |
| 0.05 mg. | D-norgestrel |
| 90.0 mg. | lactose anhydrous |
| 9.43 mg. | pregelatanized starch N.F. |
| 0.5 mg. | magnesium stearate N.F. |
| 100.015 mg. | total weight |
| | 2nd Stage 7 Tablets |
| 0.035 mg. | 17α-ethinylestradiol |
| 0.075 mg. | D-norgestrel |
| 87.70 mg. | lactose anhydrous |
| 11.69 mg. | pregelatanized starch N.F. |
| 0.5 mg. | magnesium stearate N.F. |
| 100.000 mg. | total weight |
| | 3rd Stage 7 Tablets |
| 0.035 mg. | 17α-ethinylestradiol |
| 0.100 mg. | D-norgestrel |
| 89.5 mg. | lactose anhydrous |
| 9.88 mg. | pregelatanized starch N.F. |
| 0.5 mg. | magnesium stearate N.F. |
| 100.015 mg. | total weight |

EXAMPLE 7

Composition of a tablet for each stage:

| | 1st Stage 7 Tablets |
|---|---|
| 0.035 mg. | 17α-ethinylestradiol |
| 0.025 mg. | D-norgestrel |
| 90.00 mg. | lactose anhydrous |
| 9.45 mg. | pregelatanized starch N.F. |
| 0.50 mg. | magnesium stearate N.F. |
| 100.000 mg. | total weight |
| | 2nd Stage 7 Tablets |
| 0.035 mg. | 17α-ethinylestradiol |
| 0.038 mg. | D-norgestrel |
| 87.70 mg. | lactose anhydrous |
| 11.74 mg. | pregelatanized starch N.F. |
| 0.50 mg. | magnesium stearate N.F. |
| 100.013 mg. | total weight |
| | 3rd Stage 7 Tablets |
| 0.035 mg. | 17α-ethinylestradiol |
| 0.050 mg. | D-norgestrel |
| 89.500 mg. | lactose anhydrous |
| 9.93 mg. | pregelatanized starch N.F. |
| 0.50 mg. | magnesium stearate N.F. |
| 100.015 mg. | total weight |

EXAMPLE 8

Composition of a tablet for each stage:

| | 1st Stage 7 Tablets |
|---|---|
| 0.035 mg. | 17α-ethinylestradiol |
| 0.090 mg. | norgestimate |
| 90.200 mg. | lactose anhydrous |
| 9.18 mg. | pregelatanized starch N.F. |
| 0.50 mg. | magnesium stearate N.F. |
| 100.005 mg. | total weight |
| | 2nd Stage 7 Tablets |
| 0.035 mg. | 17α-ethinylestradiol |
| 0.100 mg. | norgestimate |
| 90.150 mg. | lactose anhydrous |
| 9.23 mg. | pregelatanized starch N.F. |
| 0.50 mg. | magnesium stearate N.F. |
| 100.015 mg. | total weight |
| | 3rd Stage 7 Tablets |
| 0.035 mg. | 17α-ethinylestradiol |
| 0.125 mg. | norgestimate |
| 90.115 mg. | lactose anhydrous |
| 9.230 mg. | pregelatanized starch N.F. |
| 0.500 mg. | magnesium stearate N.F. |
| 100.005 mg. | total weight |

CLINICAL TESTS

EXAMPLE 9

A preparation according to Example 1 was administered in three separate studies to a total of 656 women of child-bearing age. Subjects meeting the selection criteria were administered the contraceptive formulation on a regimen of 21 days on medication and 7 days off for up to 12 cycles.

The preparation was shown to be highly efficacious in preventing pregnancy. In each study the bleeding pattern consistently showed a decrease in the incidence of mid-cycle breakthrough bleeding and/or spotting.

Having described the invention in specific detail and exemplified the manner in which it may be carried into practice, it will be apparent to those skilled in the art that innumerable variations, applications, modifications, and extensions of the basic principles involved may be made without departing from its spirit or scope. It is to be understood that the foregoing is merely exemplary and the present invention is not to be limited to the specific form or arrangements of parts herein described and shown.

I claim:

1. A method of contraception which comprises administering for 21 successive days to a female of childbearing age a combination of an estrogen and a progestogen in a low but contraceptively effective daily dosage corresponding in estrogenic activity to 0.02–0.05 mg of 17α-ethinylestradiol and in progestogenic activity to 0.065–0.75 mg of norethindrone for 5–8 days; for the next 7–11 days an estrogen daily dosage equal to 0.02–0.05 mg of 17α-ethinylestradiol and in progestogenic activity to 0.250–1.0 mg of norethindrone; and for the next 3–7 days an estrogen daily dosage equal to 0.02–0.05 mg of 17α-ethinylestradiol and in progestogenic activity 0.35–2.0 mg of norethindrone; followed by 6–8 days without estrogen and progestogen administration, provided that the estrogen daily dosage is the same for each period.

2. The method of claim 1 wherein the estrogen and progestogen are administered orally and the period specified in each phase is seven days.

3. The method of claim 2 wherein the estrogen and progestogen are administered in admixture.

4. The method of claim 1 wherein the progestogen is selected from the group consisting of D-norgestrel, $\Delta^{15}$ levonorgestrel, $\Delta^{15}$ levonorgestrel acetate, $\Delta^{15}$ levonorgestrel acetate oxime, norethindrone, progesterone and D-17β-acetoxy-13β-ethyl-17α-ethinyl-gon-4-en-3-one oxime.

5. The method of claim 1 wherein the estrogen is selected from the group consisting of 17α-ethinylestradiol, mestranol, estrone, estrone sulfate piperazine salt, estradiol and estriol.

6. The method of claim 3 wherein the estrogen is 17α-ethinylestradiol and the progestogen is norethindrone.

7. The method of claim 3 wherein the estrogen is 17α-ethinylestradiol 3-methyl ether and the progestogen is norethindrone.

8. The method of claim 1 wherein the estrogen is 17α-ethinylestradiol and the progestogen is D-17β-acetoxy-13β-ethyl-17α-ethinyl-gon-4-en-3-one oxime.

9. The method of claim 1 wherein the estrogen is 17α-ethinylestradiol 3-methyl ether and the progestogen is D-17β-acetoxy-13β-ethyl-17α-ethinyl-gon-4-en-3-one oxime.

10. The method of claim 6 wherein the estrogen daily dosage is 0.035 mg for each 7 day period and the progestogen daily dosage is 0.5 mg for the first 7 days, 0.75 mg for the second 7 days and 1.0 mg for the third 7 days.

11. The contraception method of claim 1 which comprises administering for 21 successive days to a female of childbearing age a combination of 17α-ethinylestradiol and norethindrone in a contraceptively effective daily dosage corresponding to 0.035 mg of 17α-ethinylestradiol and 0.50 mg of norethindrone for 7 days a daily dosage equal to 0.035 mg of 17α-ethinylestradiol and 0.75 mg of norethindrone; and for the next 7 days a daily dosage equal to 0.035 mg of 17α-ethinylestradiol and 1.0 mg of norethindrone; followed by 7 days without estrogen and progestogen administration.

12. The contraception method of claim 1 which comprises administering for 21 successive days to a female of childbearing age a combination of 17α-ethinylestradiol and D-17β-acetoxy-13β-ethyl-17α-ethinyl-gon-4-en-3-one oxime in a contraceptively effective daily dosage corresponding to 0.035 mg of 17α-ethinylestradiol and 0.180 mg of D-17β-acetoxy-13β-ethyl-17α-ethinyl-gon-4-en-3-one oxime for 7 days; for the next 7 days a daily dosage equal to 0.035 mg of 17α-ethinylestradiol and 0.215 mg of D-17β-acetoxy-13β-ethyl-17α-ethinyl-gon-4-en-3-one oxime; and for the next 7 days a daily dosage equal to 0.035 mg of 17α-ethinylestradiol and 0.250 mg of D-17β-acetoxy-13β-ethyl-17α-ethinyl-gon-4-en-3-one oxime; followed by 7 days without estrogen and progestogen administration.

13. A triphasic oral contraceptive unit consisting of 21 separate dosage units, adapted for successive daily oral administration comprising:

7 dosage units containing, in admixture with a pharmaceutically acceptable carrier, a combination of an estrogen and a progestogen at contraceptively effective dosages corresponding in activity to 0.02–0.05 mg of 17α-ethinylestradiol and in progestogenic activity to 0.065–0.75 mg of norethindrone as the first phase; followed by 7 dosage units containing in admixture with a pharmaceutically acceptable carrier, a combination of an estrogen at a contraceptively effective dosage corresponding in activity to 0.02–0.05 mg of 17α-ethinylestradiol and in progestogenic activity to 0.25–1.0 mg of norethindrone as the second phase; followed by 7 dosage units containing in admixture with a pharmaceutically acceptable carrier, a combination of an estrogen at a contraceptively effective dosage corresponding to 0.02–0.05 mg of 17α-ethinylestradiol and in progestogenic activity to 0.35–2.0 mg of norethindrone as the third phase, and optionally containing 7 dosage units free of estrogen and progestogen; provided that the estrogen daily dosage is the same in all three phases.

14. The unit according to claim 13 wherein the dosage units are in the form of tablets.

15. The unit according to claim 13 wherein the estrogen is selected from the group consisting of 17α-ethinylestradiol, mestranol, estrone, estrone sulfate, estrone sulfate piperazine salt, estradiol and estriol.

16. The unit according to claim 14 wherein the estrogen is 17α-ethinylestradiol.

17. The unit according to claim 13 wherein the estrogen is 17α-ethinylestradiol 3-methyl ether.

18. The unit according to claim 13 wherein the progestogen is selected from the group consisting of D-norgestrel, $\Delta^{15}$ levonorgestrel, $\Delta^{15}$ levonorgestrel acetate, $\Delta^{15}$ levonorgestrel acetate oxime, norethindrone, progesterone and D-17β-acetoxy-13β-ethyl-17α-ethinyl-gon-4-en-3-one oxime.

19. The unit according to claim 18 wherein the progestogen is norethindrone.

20. The unit according to claim 18 wherein the progestogen is D-17β-acetoxy-13β-ethyl-17α-ethinyl-gon-4-en-3-one oxime.

21. The unit according to claim 13 wherein the estrogen is 17α-ethinylestradiol 3-methyl ether and the progestogen is norethindrone.

22. The unit according to claim 13 wherein the estrogen is 17α-ethinylestradiol 3-methyl ether and the progestogen is D-17β-acetoxy-13β-ethyl-17α-ethinyl-gon-4-en-3-one oxime.

23. A composition according to claim 13 wherein the estrogen daily dosage in all three phases is equivalent to 0.035 mg of 17α-ethinylestradiol; and the progestogen daily dosage is equivalent to 0.50 mg of norethindrone in the first phase, 0.75 mg of norethindrone in the second phase and 1.0 mg of norethindrione in the third phase.

24. A composition according to claim 13 wherein the estrogen daily dosage in all three phases is equivalent to 0.035 mg of 17α-ethinylestradiol; and the progestogen daily dosage is equivalent to 0.180 mg of D-17β-acetoxy-13β-ethyl-17α-ethinyl-gon-4-en-3-one oxime in the first phase, 0.215 mg of D-17β-acetoxy-13β-ethyl-17α-ethinyl-gon-4-en-3-one oxime in the second phase and 0.250 mg of D-17β-acetoxy-13β-ethyl-17α-ethinyl-gon-4-en-3-one oxime in the third phase.

25. A triphasic oral contraceptive unit consisting of 21 separate dosage units, adapted for successive daily oral administration comprising:
5-8 dosage units containing, in admixture with a pharmaceutically acceptable carrier, a combination of an estrogen and a progestogen at contraceptively effective dosages corresponding in activity to 0.02-0.05 mg of 17α-ethinylestradiol and in progestogenic activity to 0.065-0.75 mg of norethindrone as the first phase; followed by 7-11 dosage units containing in admixture with a pharmaceutically acceptable carrier, a combination of an estrogen at a contraceptively effective dosage corresponding in activity to 0.02-0.05 mg of 17α-ethinylestradiol and in progestogenic activity to 0.25-1.0 mg of norethindrone as the second phase; followed by 3-7 dosage units containing in admixture with a pharmaceutically acceptable carrier, a combination of an estrogen at a contraceptively effective dosage corresponding to 0.02-0.05 mg of 17α-ethinylestradiol and in progestogenic activity to 0.35-2.0 mg of norethindrone as the third phase, and optionally containing 6-8 dosage units free of estrogen and progestogen; provided that the estrogen daily dosage is the same in all three phases.

* * * * *

UNITED STATES PATENT AND TRADEMARK OFFICE
CERTIFICATE OF CORRECTION

PATENT NO.  :   4,628,051

DATED       :   December 9, 1986

INVENTOR(S) :   Samuel A. PASQUALE

It is certified that error appears in the above-identified patent and that said Letters Patent is hereby corrected as shown below:

On the title page, after item [73], "* Notice" should read as follows:
-- The portion of the term of this patent subsequent to July 23, 2002 has been disclaimed. --.

Signed and Sealed this

Sixth Day of July, 1993

Attest:

MICHAEL K. KIRK

*Attesting Officer*    *Acting Commissioner of Patents and Trademarks*